… [54] DIARYL-PYRIDYL-IMIDAZOLE METHANES FOR TREATING MYCOTIC INFECTIONS

[75] Inventors: Wilfried Draber; Manfred Plempel; Karl Heinz Büchel, all of Wuppertal, Germany

[73] Assignee: Bayer Aktiengesellschaft, Germany

[22] Filed: Mar. 11, 1975

[21] Appl. No.: 557,354

Related U.S. Application Data

[62] Division of Ser. No. 367,849, June 7, 1973, Pat. No. 3,910,936.

[30] Foreign Application Priority Data

June 15, 1972 Germany............................ 2229128

[52] U.S. Cl. .............................................. 424/263
[51] Int. Cl.² ......................................... A61K 31/44
[58] Field of Search ................................... 424/263

Primary Examiner—Jerome D. Goldberg

[57] ABSTRACT

Diaryl-pyridyl-imidazolyl methanes of the formula

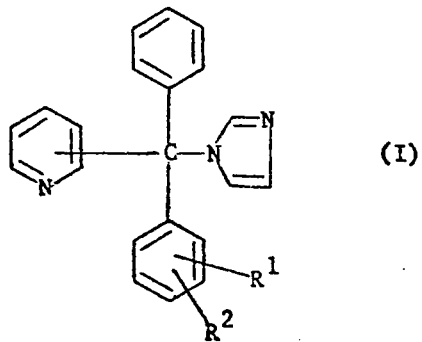

and pharmaceutically acceptable non-toxic salts thereof, wherein $R^1$ and $R^2$ are the same or different alkyl of 1 to 4 carbon atoms, are produced either by
a. reacting a (dialkylphenyl-phenyl-pyridyl)-methanol of the formula

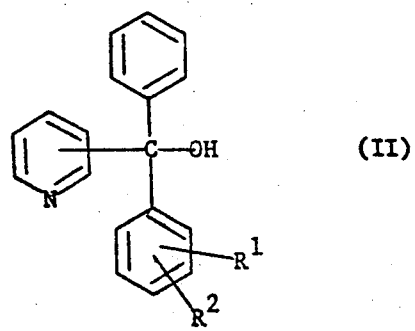

wherein $R^1$ and $R^2$ are as above defined, with thionyl-bis-imidazole in the presence of an inert organic diluent at a temperature of from −20° C to about 150° C; or b. reacting a (dialkylphenyl-phenyl-pyridyl)-methyl halide of the formula

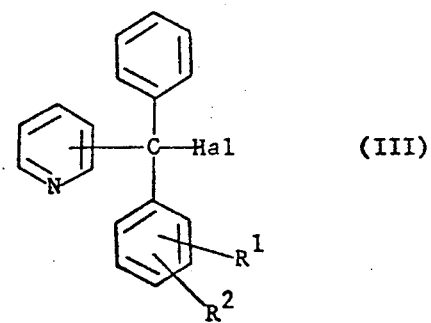

wherein $R^1$ and $R^2$ are as above defined and Hal is chlorine or bromine, with imidazole in the presence of an acid binding agent at a temperature of from 20° C to about 180°C. The diaryl-pyridyl-imidazole methanes of the present invention are useful for their antimycotic activity.

50 Claims, No Drawings

DIARYL-PYRIDYL-IMIDAZOLE METHANES FOR TREATING MYCOTIC INFECTIONS

This is a division of parent application Ser. No. 367,849 filed June 7, 1973, which issued as U.S. Pat. No. 3,910,936 on Oct. 7, 1975.

The present invention relates to diarylimidazolyl-methane compounds, to processes for their production, pharmaceutical compositions using said compounds as the active ingredient and to methods of treating mycosis in humans and animals which comprises administering said compounds.

More particularly, the present invention relates to diphenyl-pyridyl-imidazolyl methanes containing two alkyl substituents in one of the two phenyl rings.

It is known in the art that certain N-tritylimidazoles are active against plant-pathogenic fungi (U.S. Pat. No. 3,321,366). It is furthermore known that certain N-tritylimidazoles are active against human-pathogenic fungi such as epidermatophytes and other dermatophytes as well as blastomyces and biphase fungi (Belgian Patent Specification No. 720,801; U.S. Pat. Nos. 3,655,899; 3,655,900; 3,657,442; 3,657,445; 3,658,956; 3,660,576; and 3,660,577).

It is also known in the art that mono-substituted diaryl-pyridyl-imidazolyl-methanes such as 1-(4-fluorophenyl-phenyl-2-pyridyl)-methyl-imidazole and 1-(3-trifluoromethyl-phenyl-phenyl-2-pyridyl)-methyl-imidazole are useful as antimycotic agents (See German Offenlegungsschriften Nos. 1,770,939 and 2,009,020). However, the activity of those compounds both in vitro and in vivo against dermatophytes and especially against varieties of Trichophyton is generally unsatisfactory. The compounds of the present invention, by contrast, are particularly useful against Trichophyton infections.

The present invention, therefore, is concerned with diaryl-pyridyl-imidazolyl-methanes of the formula

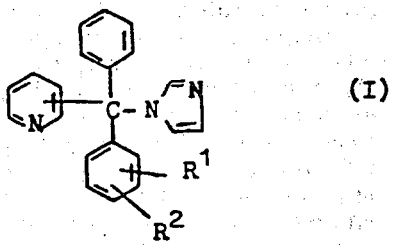

and pharmaceutically acceptable non-toxic salts thereof, wherein $R^1$ and $R^2$ are the same or different alkyl of 1 to 4 carbon atoms.

The compounds of the present invention may be produced by:

a. reacting a (dialkylphenyl-phenyl-pyridyl)-methanol of the formula

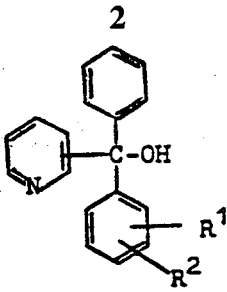

wherein $R^1$ and $R^2$ are as above defined, with thionyl-bis-imidazole in the presence of an inert organic diluent at a temperature of from $-20°$ C to about $150°$ C; or b. reacting a (dialkylphenyl-phenyl-pyridyl)-methyl halide of the formula

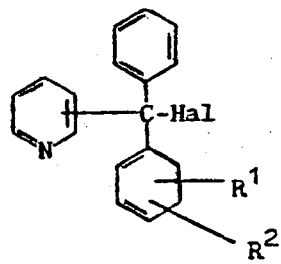

wherein $R^1$ and $R^2$ are as above defined and Hal is chloro or bromo, with imidazole in the presence of an acid binding agent at a temperature of from about $20°$ C to about $180°$ C The two processes (a) and (b) of the present invention will hereinafter be referred to as Process Variants (a) and (b) respectively.

As stated above, the compounds of the present invention are active against dermatophytes, especially Trichophyton. It was surprisingly discovered that the 1-(dialkylphenyl-pyridyl-phenyl)-methyl-imidazoles of the present invention showed a higher level of activity against dermatophytes, and especially Trichophyton, than 1-(4-fluorophenyl-phenyl-2-pyridyl)-methyl imidazole and 1-(3-trifluoromethylphenyl-phenyl-2-pyridyl)-methyl imidazole, which are, from a purely chemical standpoint, the closest compounds of the prior art.

According to one embodiment of the presnt invention, the pyridyl moiety is linked with the methane carbon atom at the 2-position of the pyridyl ring. According to another embodiment of the present invention, the pyridyl moiety is linked to the methane carbon atom at the 4-position of the pyridyl ring.

According to a further embodiment of the present invention, $R^1$ and $R^2$ are preferably each a methyl group.

According to a further embodiment of the present invention, $R^1$ is preferably in the 2- or 3-position of the phenyl ring. According to a further embodiment of the present invention, $R^2$ is preferably in the 3-, 4-, 5- or 6-position of the phenyl ring.

According to a further embodiment of the present invention, $R^1$ and $R^2$ are in different positions on the phenyl ring.

If (2,3-dimethylphenyl-phenyl-2-pyridyl)-methanol and thionyl-bis-imidazole are used as starting materials, the course of the reaction in Process Variant (a) can be represented by the following equation:

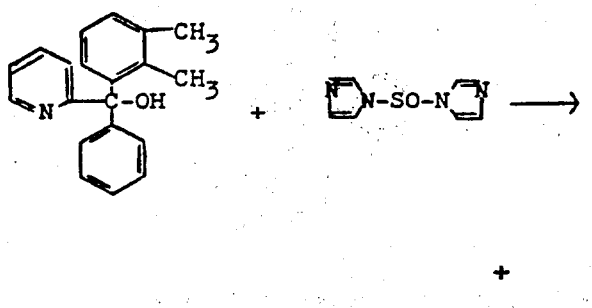 + 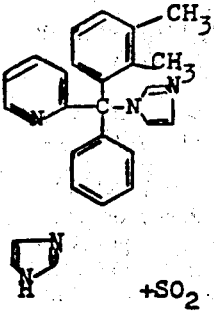 →

If (2,3-dimethylphenyl-phenyl-2-pyridyl)-methyl chloride and imidazole are used as the starting materials, the course of the reaction in Process Variant (b) can be represented by the following equation:

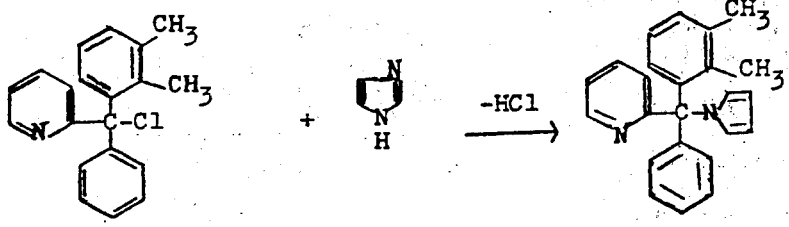 + 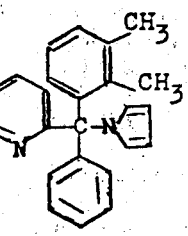 —HCl→

The formulae (II) and (III) provide a general definition of the starting compounds for the Process Variants (a) and (b). In the formulae (I), (II) and (III), $R^1$ and $R^2$ individually and independently of one another represent straight-chain or branched alkyl groups of 1 to 4 carbon atoms, and at least one of them is preferably methyl; Hal in the formula (III) preferably represents a chlorine or bromine atom.

The following alcohols and halides of the formulae (II) and (III) are representative of the starting materials utilizable according to the present invention:

(3,4-dimethylphenyl-phenyl-2-pyridyl)-methyl chloride,
(3,4-dimethylphenyl-phenyl-2-pyridyl)-methanol,
(3,4-dimethylphenyl-phenyl-4-pyridyl)-methyl chloride,
(3,4-dimethylphenyl-phenyl-4-pyridyl)-methanol,
(2,3-dimethylphenyl-phenyl-2-pyridyl)-methyl chloride,
(2,3-dimethylphenyl-phenyl-4-pyridyl)-methyl chloride,
(2,3-dimethylphenyl-phenyl-2-pyridyl)-methanol,
(2,3-dimethylphenyl-phenyl-4-pyridyl)-methanol,
(2,4-dimethylphenyl-phenyl-2-pyridyl)-methyl chloride,
(2,4-dimethylphenyl-phenyl-2-pyridyl)-methanol,
(2,4-dimethylphenyl-phenyl-4-pyridyl)-methyl chloride,
(2,4-dimethylphenyl-phenyl-4-pyridyl)-methanol,
(2,5-dimethylphenyl-phenyl-2-pyridyl)-methyl chloride,
(2,5-dimethylphenyl-phenyl-2-pyridyl)-methanol,
(2,5-dimethylphenyl-phenyl-4-pyridyl)-methyl chloride,
(2,5-dimethylphenyl-phenyl-4pyridyl)-methanol,
(2,6-dimethylphenyl-phenyl-2-pyridyl)-methyl chloride and
(2,6-dimethylphenyl-phenyl-4-pyridyl)-methanol.

The alcohols and halides which can be used as starting materials in the process according to the invention are in part known or can be produced by known methods (see Journal of the American Chemical Society, volume 70, pages 4001–4009 (1948) and volume 79, pages 472–480 (1957); Journal of Organic Chemistry, volume 26, pages 4084–4088 (1961); U.S. Pat. Nos. 3,396,224 and 2,624,739).

The pharmaceutically acceptable non-toxic salts of the present invention are preferably those obtained from such acids as the hydrogen halide acids (for example, hydrochloric acid and hydrobromic acid, especially hydrochloric acid), phosphoric acids, nitric acid, monofunctional and bifunctional carboxylic acids, hydroxycarboxylic acids (for example, acetic acid, maleic acid, succinic acid, fumaric acid, tartaric acid, citric acid, salicylic acid, sorbic acid and lactic acid), and 1,5-naphthalene-disulphonic acid. Thus, the preferred salts, according to the present invention are the hydrochloride, hydrobromide, phosphate, nitrate, carboxylates, hydroxycarboxylates, (for example, acetate, maleate, succinate, fumarate, tartrate, citrate, salicylate, sorbate, lactate) and 1,5-naphthalene-disulphonate.

In Process Variant (a) the diluent is preferably a well-dried (preferably anhydrous) organic solvent, which is inert to the reaction. Preferred solvents include hydrocarbons (such as benzene and toluene), chlorinated hydrocarbons (such as chlorobenzene, methylene chloride, chloroform and carbon tetrachloride), ketones (such as acetone and methyl ethyl ketone), ethers (such as petroleum ether, diethyl ether and tetrahydrofurane), nitriles (such as acetrontrile), sulphoxides (such as dimethyl-sulphoxide), and amides (such as dimethylformamide). Anhydrous acetonitrile is particularly preferred as the solvent.

The reaction temperature in Process Variant (a) can be varied within a substantial range of −20° C to 150° C. Advantageously, the reaction is carried out at 0° C to 50° C.

In carrying out Process Variant (a) according to the invention, 1 to 3 moles of thionyl-bis-imidazole are generally used per 1 mol of alcohol of the general formula (II). A larger excess of thionyl-bis-imidazole is only necessary if a badly dried solvent is employed. The reaction usually takes between 1 and 10 hours. The reaction product precipitates after partially distilling off the solvent and can be filtered off or isolated in accordance with the customary methods.

In Process Variant (b), polar organic solvents may be used. These include, for example, nitriles (such as acetonitrile), sulphoxides (such as dimethylsulphoxide), formamides (such as dimethyl formamide), ketones (such as acetone), and ethers (such as diethyl ether and tetrahydrofurane). However, the reaction is preferably carried out without diluents.

The reaction of Process Variant (b) is carried out in the presence of an acid-binding agent. Preferably, an appropriate excess of imidazole is used as acid-binding agent. It is, however, also possible to add any other organic acid-binding agents including those usually employed for reactions in which acids are liberated, such as lower tertiary alkylamines and aralkylamines (for example, triethylamine and dimethylbenzylamine). The reaction temperature in Process Variant (b) can be varied within a substantial range of 20° C to 180° C, preferably 50° C to 110° C.

In carrying out the Process Variant (b) according to the invention, preferably about 1 mol of imidazole and about 1 mol of acid-binding agent are employed per 1 mol of the compound of the formula (III). The compound produced can be isolated in accordance with known and customary methods.

The new free diaryl-pyridyl-imidazolyl-methanes of the formula (I) and their salts can be interconverted in any suitable manner. Methods for such interconversion are known in the art.

The following compounds are representative of those of the present invention:

Table 1

| Example No. | Compound |
|---|---|
| 1 | 1-(3,4-dimethylphenyl-phenyl-2-pyridyl)-methyl-imidazole |
| 2 | 1-(2,4-dimethylphenyl-phenyl-2-pyridyl)-methyl-imidazole |
| 3 | 1-(2,6-dimethylphenyl-phenyl-2-pyridyl)-methyl-imidazole hydrochloride |
| 4 | 1-(2,4-dimethylphenyl-phenyl-4-pyridyl)-methyl-imidazole |
| 5 | 1-(3,4-dimethylphenyl-phenyl-4-pyridyl)-methyl-imidazole |
| 6 | 1-(2,5-dimethylphenyl-phenyl-4-pyridyl)-methyl-imidazole |
| 7 | 1-(2,3-dimethylphenyl-phenyl-2-pyridyl)-methyl-imidazole |
| 8 | 1-(2,3-dimethylphenyl-phenyl-2-pyridyl)-methyl-imidazole 1,5-naphthalenedisulphonate |
| 9 | 1-(2,3-dimethylphenyl-phenyl-4-pyridyl)-methyl-imidazole |
| 10 | 1-(3,4-dimethylphenyl-phenyl-4-pyridyl)-methyl-imidazole 1,5-naphthalenedisulphonate |

The preferred compound of the present invention is 1-(2,3-dimethylphenyl-phenyl-2-pyridyl)-methyl-imidazole and salts thereof, especially the hydrochloride salt.

The compounds of the present invention show a broad spectrum of antimycotic activity. They exhibit activity against yeasts suchas Candida and Cryptococcus molds such as Aspergillus and Penicillium, and dermatophytes such as Trichophylen, Microsporon and Epidermophyton. The compounds of the present invention are particularly active against dermatophytes of the Trichophyton genus.

According to the present invention, the above compounds may be administered to both humans and animals. The compounds may be used in both the treatment and prophylaxis of dermatomycoses and systemic mycoses caused by Trichophyton mentagrophytes and other varieties of Trichophton, varieties of Microsporon, Epidermophyton floccosum blastomyces and biphase fungi, as well as molds and the above-mentioned pathogens, and also organic mycoses caused by varieties of Candida, Cryptococcus, Coccidioides, Histoplasma and Blastomyces.

In veterinary medicine the compounds of the present invention may be used, for example, against dermatomycoses, systemic mycoses and organic mycoses, especially those caused by the above-mentioned pathogens.

The present invention also comprises pharmaceutical compositions which contain a major or minor amount, e.g., 99.5% to 0.1%, and particularly 95.0% to 0.5%, of at least one diaryl-pyrimidyl-imidazolyl methane as herein defined in combination with a pharmaceutical carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain, one, two, three, four or more single doses, or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the daily dosage will be from about 500 to 9000 mg, preferably 1000 to 5400 mg. 10 to 100 mg/kg and, preferably, 20 to 60 mg/kg would be the preferred daily dosage based on the weight of the recipient. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as, for example, starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants, suchas colloidal silica, talc, magnesium stearate, calcium stearate or solid polyethylene glycol, can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and distintegrant, and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers succh as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as, for example, myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colarants, perfumes and the like can also be present. Formulations can also be administered as an aerosol, utilizing the usual propellants such as the chlorofluorohydrocarbons.

The microbiological activity of the compounds of the present invention are illustrated by the following data:

A. Determination of the antimycotic action spectrum in vitro by means of the series dilution test Sabourauds' milieu d'epreuve is used as the nutrient substrate for dermatophytes and Aspergilli, and meat-broth-glucose-bouillon is used as the the nutrient substrate for blastomyces. The incubation temperature is 28° C and the incubation time is 24 to 96 hours.

The experimental results are summarized in Table A in which:

"Known compound 1" is 1-(4-fluorophenyl-phenyl-2-pyridyl)-methylimidazole (see above), and "Known compound 2" is 1-(3-trifluoromethylphenyl-phenyl-2-pyridyl)-methylimidazole (see above).

Table A

| | Minimum Inhibitory Concentration in γ/ml of Nutrient Medium | | | |
|---|---|---|---|---|
| Compound | Trichophyton mentagrophytes | Candida albicans | Penicillium commune | Aspergillis niger |
| Known Compound 1 | <4 >2 | 4 | <4 >2 | 4 2 |
| Known Compound 2 | <4 >2 | 4 | <4 >2 | <4 >2 |
| Example No. From Table 1: | | | | |
| 1 | 0.5 | 1 | 4 | <1 |
| 2 | 0.5 | 10 | 4 | 4 |
| 3 | 0.5 | 1 | 10 | 4 |
| 4 | 0.5 | 4 | 10 | 4 |
| 5 | 0.5 | 1 | 10 | 1 |
| 6 | 0.5 | 4 | 40 | 40 |
| 7 | 0.05 | 1 | 1 | 0.1 |
| 8 | 1 | 1 | 4 | 1 |
| 9 | 0.5 | 1 | 4 | 1 |
| 10 | 10 | 1 | 4 | 4 |

9

B. Antimycotic action of the compounds according to the present invention in animal experiments Quinckeanum Trichophytosis of white mice The development of the Quinckeanum infection in mice can be completely suppressed with doses of 12.5 mg/kg of body weight, of the active compound from Example 7, given orally twice daily up to the eighth day of the infection per os.

Preparative Example (Compound No. 7)

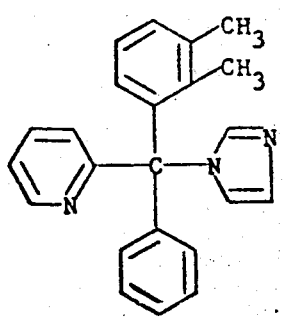

28.9 g (0.1 mol) of (2,3-dimethylphenyl-phenyl-2-pyridyl)-methanol are dissolved in 200 ml of anhydrous acetonitrile. A solution of thionyl-bis-imidazole prepared from 10.7 ml (0.15 mol) of thionyl chloride and 40.7 g (0.6 mol) of imidazole at 0° to 5° C is added dropwise thereto, under reflux cooling. The reaction is left to proceed overnight at room temperature and is completed by boiling for one hour under reflux.

To isolate the resulting imidazole compound, the excess solvent is distilled off in vacuo, the residue is treated with water, the mixture is extracted with ether and the resulting ether solution is briefly boiled up with active charcoal. After filtration, the solution is dried over sodium sulphate and the solvent is distilled off. The resulting oily residue is triturated with pentane and thereafter crystallizes throughout. Filtration yields 10.5 g (31% of theory) of 1-(2,3-dimethylphenyl-phenyl-2-pyridyl)-methyl-imidazole of melting point 151° C.

The (2,3-dimethylphenyl-phenyl-2-pyridyl)-methanol used as the starting product is obtained in a yield of 580 g (67% of theory) by reaction of 2,3-dimethylphenylmagnesium bromide, which was manufactured from 740 g (4 mols) of m-bromo-o-xylene and 97.2 g (4 mols) of magnesium filings in 1.5 liters of ether, with 549 g (3 mols) of 2-benzoylpyridine, and has a melting point of 129° C.

Table 2 below sets forth compounds representative of the present invention.

10

Table 2

| Example No. | Pyridyl | R¹ | R² | Melting Point in °C |
|---|---|---|---|---|
| 1 | 2- | 3-CH₃ | 4-CH₃ | 96 |
| 2 | 2- | 2-CH₃ | 4-CH₃ | 158 |
| 3 | 2- | 2-CH₃ | 6-CH₃ | Hydrochloride, 120 |
| 4 | 4- | 2-CH₃ | 4-CH₃ | 168 |
| 5 | 4- | 3-CH₃ | 4-CH₃ | 122 |
| 6 | 4- | 2-CH₃ | 5-CH₃ | 129 |
| 7 | 2- | 2-CH₃ | 3-CH₃ | 151 |
| 8 | 2- | 2-CH₃ | 3-CH₃ | 1,5-Naphthalene disulfonate 168 |
| 9 | 4- | 2-CH₃ | 3-CH₃ | 154 |
| 10 | 4- | 3-CH₃ | 4-CH₃ | 1,5-Naphthalene disulfonate 238 |

Table 3 below sets forth the specific dialkylphenyl-phenyl-pyridyl methanol which is reacted with thionyl-bis-imidazole in the presence of an inert inorganic diluent at from −20° C to 150° C to produce the particular dialkylphenyl-phenyl-pyridyl-imidazole methane set forth in Table 2.

Table 3

Dialkylphenyl-phenyl-pyridyl-imidazole-methane

| Example No. | |
|---|---|
| 1 | 3,4-dimethylphenyl-phenyl-2-pyridyl-methanol |
| 2 | 2,4-dimethylphenyl-phenyl-2-pyridyl-methanol |
| 3 | 2,6-dimethylphenyl-phenyl-2-pyridyl-methanol |
| 4 | 2,4-dimethylphenyl-phenyl-4-pyridyl-methanol |
| 5 | 3,4-dimethylphenyl-phenyl-4-pyridyl-methanol |
| 6 | 2,5-dimethylphenyl-phenyl-4-pyridyl-methanol |
| 7 | 2,3-dimethylphenyl-phenyl-2-pyridyl-methanol |
| 8 | 2,3-dimethylphenyl-phenyl-2-pyridyl-methanol |
| 9 | 2,3-dimethylphenyl-phenyl-4-pyridyl-methanol |
| 10 | 3,4-dimethylphenyl-phenyl-4-pyridyl-methanol |

In the case of Examples 3, 8 and 10, the free base produced is reacted with the appropriate acid, namely, hydrochloric (Example 3) or naphthalene disulfonic (Examples 8 and 10), to produce the corresponding hydrochloride (Example 3) and 1,5-naphthalene disulfonate (Examples 8 and 10).

The hydrochloride salt of the compound of Example 7 is produced by reacting the free base (compound of Example 7) with hydrochloric acid.

Table 4 below sets forth the specific dialkylphenyl-phenyl-pyridyl-methyl halide (preferably the chloride or bromide) which is reacted with imidazole in the presence of an acid binding agent at from 20° C to 180° C to produce the particular dialkylphenyl-phenyl-pyridyl-imidazole methane set forth in Table 2.

Table 4

| Example No. | Dialkylphenyl-phenyl-pyridyl-methyl-halide |
|---|---|
| 1 | 3,4-dimethylphenyl-phenyl-2-pyridyl-methyl chloride (or bromide) |
| 2 | 2,4-dimethylphenyl-phenyl-2-pyridyl-methyl chloride (or bromide) |
| 3 | 2,6-dimethylphenyl-phenyl-2-pyridyl-methyl chloride (or bromide) |
| 4 | 2,4-dimethylphenyl-phenyl-4-pyridyl-methyl chloride (or bromide) |
| 5 | 3,4-dimethylphenyl-phenyl-4-pyridyl-methyl chloride (or bromide) |
| 6 | 2,5-dimethylphenyl-phenyl-4-pyridyl-methyl chloride (or bromide) |
| 7 | 2,3-dimethylphenyl-phenyl-2-pyridyl-methyl chloride (or bromide) |
| 8 | 2,3-dimethylphenyl-phenyl-2-pyridyl-methyl chloride (or bromide) |
| 9 | 2,3-dimethylphenyl-phenyl-4-pyridyl-methyl chloride (or bromide) |
| 10 | 3,4-dimethylphenyl-phenyl-4-pyridyl-methyl chloride (or bromide) |

In the case of Examples 3, 8 and 10, the free base produced is reacted with the appropriate acid, namely, hydrochloric (Example 3) or 1,5-naphthalene disulfonic (Examples 8 and 10), to produce the corresponding hydrochloride (Example 3) and 1,5-naphthalene disulfonate (Examples 8 and 10).

The hydrochloride salt of the compound of Example 7 is produced by reacting the free base (compound of Example 7) with hydrochloric acid.

What is claimed is:

1. An antimycotic composition for treating mycotic infections in humans and animals which comprises an antimycotically effective amount of a compound of the formula

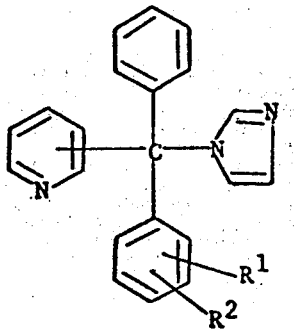

or a pharmaceutically acceptable, non-toxic salt thereof wherein $R^1$ and $R^2$ are the same or different alkyl of 1 to 4 carbon atoms, in combination with a pharmaceutically acceptable, nontoxic, inert diluent or carrier.

2. A composition according to claim 1 wherein the compound is in the form of a salt and the salt is selected from the group consisting of the hydrochloride, the hydrobromide, the phosphate, the nitrate, the acetate, the maleate, the succinate, the fumarate, the tartrate, the citrate, the salicylate, the sorbate, the lactate, and the 1,5-naphthalene-disulphonate.

3. A composition according to claim 1 wherein the pyridyl moiety is linked to the methane carbon atom at the 2-position.

4. A composition according to claim 1 wherein the pyridyl moiety is linked to the methane carbon atom at the 4-position.

5. A composition accordig to claim 1 wherein $R^1$ and $R^2$ are each methyl.

6. A composition according to claim 1 wherein $R^1$ is in the 2- or 3-position.

7. A composition according to claim 1 wherein $R^2$ is in the 3-, 4-, 5- or 6-position.

8. A composition according to claim 3 wherein $R^1$ is in the 2- or 3-position and $R^2$ is in the 3-, 4-, 5- or 6-position, but $R^1$ and $R^2$ are not both in the 3-position.

9. A composition according to claim 4 wherein $R^1$ is in the 2- or 3-position and $R^2$ is in the 3-, 4-, 5- or 6-position, but $R^1$ and $R^2$ are not both in the 3-position.

10. A composition according to claim 5 wherein $R^1$ is in the 2- or 3-position and $R^2$ is in the 3-, 4-, 5- or 6-position, but $R^1$ and $R^2$ are not both in the 3-position.

11. The composition according to claim 1 wherein the compound is 1-(3,4-dimethylphenyl-phenyl-2-pyridyl)-methyl-imidazole.

12. The composition according to claim 1 wherein the compound is 1-(2,4-dimethylphenyl-phenyl-2-pyridyl)-methyl-imidazole.

13. The composition according to claim 1 wherein the compound is 1-(2,6-dimethylphenyl-phenyl-2-pyridyl)-methyl-imidazole or the hydrochloride salt thereof.

14. The composition according to claim 1 wherein the compound is 1-(2,4-dimethylphenyl-phenyl-4-pyridyl)-methyl-imidazole.

15. The composition according to claim 1 wherein the compound is 1-(3,4-dimethylphenyl-phenyl-4-pyridyl)-methyl-imidazole.

16. The composition according to claim 1 wherein the compound is 1-(2,5-dimethylphenyl-phenyl-4-pyridyl)-methyl-imidazole.

17. The composition according to claim 1 wherein the compound is 1-(2,3-dimethylphenyl-phenyl-2-pyridyl)-methyl-imidazole.

18. The composition according to claim 1 wherein the compound is the hydrochloride salt of 1-(2,3-dimethylphenyl-phenyl-2-pyridyl)-methylimidazole.

19. The composition according to claim 1 wherein the compound is the 1,5-naphthalene-disulphonate salt of 1-(2,3-dimethylphenyl-phenyl-2-pyridyl)-methyl-imidazole.

20. The composition according to claim 1 wherein the compound is 1-(2,3-dimethylphenyl-phenyl-4-pyridyl)-methyl-imidazole.

21. The composition according to claim 1 wherein the compound is 1-(3,4-dimethylphenyl-phenyl-4-pyridyl)-methyl-imidazole or the 1,5-naphthalene-disulphonate salt thereof.

22. A composition according to claim 1 in oral administration form.

23. A composition according to claim 1 in parenteral administration form.

24. A composition according to claim 1 in a form suitable for topical application.

25. A method of treating mycotic infections in humans and animals which comprises administering to a human or animal an antimycotically effective amount of a compound of the formula

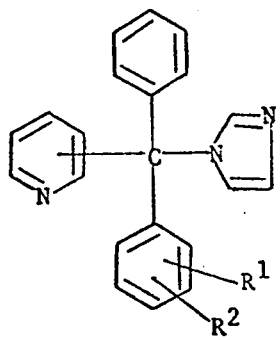

or a pharmaceutically acceptable, non-toxic salt thereof wherein $R^1$ and $R^2$ are the same or different alkyl of 1 to 4 carbon atoms.

26. A method according to claim 25 wherein the administration is oral.

27. A method according to claim 25 wherein the administration is parenteral.

28. A method according to claim 25 wherein the administration is by topical application to the infected area.

29. A method according to claim 25 wherein the antimycotically effective amount is 10 to 100 mg/kg per day.

30. A method according to claim 29 wherein the amount is from 20 to 60 mg/kg per day.

31. A method according to claim 25 wherein the compound is in the form of a salt and the salt is selected from the group consisting of the hydrochloride, the hydrobromide, the phosphate, the nitrate, the acetate, the maleate, the succinate, the fumarate, the tartrate, the citrate, the salicylate, the sorbate, the lactate, and the 1,5-naphthalene-disulphonate.

32. A method according to claim 25 wherein the pyridyl moiety is linked to the methane carbon atom at the 2-position.

33. A method according to claim 25 wherein the pyridyl moiety is linked to the methane carbon atom at the 4-position.

34. A method according to claim 25 wherein $R^1$ and $R^2$ are each methyl.

35. A method according to claim 25 wherein $R^1$ is in the 2- or 3-position.

36. A method according to claim 25 wherein $R^2$ is in the 3-, 4-, 5- or 6position.

37. A method according to claim 32 wherein $R^1$ is in the 2- or 3-position and $R^2$ is in the 3-, 4-, 5- or 6-position, but $R^1$ and $R^2$ are not both in the 3-position.

38. A method according to claim 33 wherein $R^1$ is in the 2- or 3-position and $R^2$ is in the 3-, 4-, 5- or 6-position, but $R^1$ and $R^2$ are not both in the 3-position.

39. A method according to claim 34 wherein $R^1$ is in the 2- or 3-position and $R^2$ is in the 3-, 4-, 5- or 6-position, but $R^1$ and $R^2$ are not both in the 3-position.

40. A method according to claim 25 wherein the compound is 1-(3,4-Dimethylphenyl-phenyl-2-pyridyl)-methyl-imidazole.

41. A method according to claim 25 wherein the compound is 1-(2,4-dimethylphenyl-phenyl-2-pyridyl)-methyl-imidazole.

42. A method according to claim 25 wherein the compound is 1-(2,6-dimethylphenyl-phenyl-2-pyridyl)-methyl-imidazole or the hydrochloride salt thereof.

43. A method according to claim 25 wherein the compound is 1-(2,4-dimethylphenyl-phenyl-4-pyridyl)-methyl-imidazole.

44. A method according to claim 25 wherein the compound is 1-(3,4-dimethylphenyl-phenyl-4-pyridyl)-methyl-imidazole.

45. A method according to claim 25 wherein the compound is 1-(2,5-dimethylphenyl-phenyl-4-pyridyl)-methyl-imidazole.

46. A method according to claim 25 wherein the compound is 1-(2,3-dimethylphenyl-phenyl-2-pyridyl)-methyl-imidazole.

47. A method according to claim 25 wherein the compound is 1-(2,3-dimethylphenyl-phenyl-2-pyridyl)-methyl-imidazole.

48. A method according to claim 25 wherein the compound is the 1,5-naphthalene-disulphonate salt of 1-(2,3-dimethylphenyl-phenyl-2-pyridyl)-methyl-imidazole.

49. A method according to claim 25 wherein the compound is 1-(2,3-dimethylphenyl-phenyl-4-pyridyl)-methyl-imidazole.

50. A method according to claim 25 wherein the compound is 1-(3,4-dimethylphenyl-phenyl-4-pyridyl)-methyl-imidazole or the 1,5-naphthalene-disulphonate salt thereof.

* * * * *